US00PP08079P

United States Patent [19]

Stravers

[11] Patent Number: Plant 8,079

[45] Date of Patent: Dec. 29, 1992

[54] GERBERA PLANT NAMED TERSOMKA

[75] Inventor: Lambertus J. M. Stravers, Kudelstaart, Netherlands

[73] Assignee: Terra Nigra BV, De Kwakel, Netherlands

[21] Appl. No.: 696,595

[22] Filed: May 7, 1991

[30] Foreign Application Priority Data

Nov. 2, 1990 [NL] Netherlands ..... 1168

[51] Int. Cl.[5] ..... A01H 5/00

[52] U.S. Cl. ..... Plt./68.1

[58] Field of Search ..... Plt./68

*Primary Examiner*—James R. Feyrer

*Attorney, Agent, or Firm*—Foley & Lardner

[57] ABSTRACT

A new and distinct cultivar of Gerbera plant named Tersomka, characterized by its single type flower and cup shaped flower form; cream ray floret color; dark purple disc florets; cream perianth lobes and relatively small diameter flower head.

1 Drawing Sheet

The present invention comprises a new and distinct cultivar of Gerbera plant, botanically known as *Gerbera jamesonii,* and referred to by the cultivar name Tersomka.

Tersomka was originated from a hybridization made in a controlled breeding program in De Kwakel, The Netherlands in 1989 under the supervision of the inventor Lambertus J. M. Stravers.

The female parent was a cultivar designated M89.2. The male parent was a cultivar designated M89.27. The new cultivar was discovered and selected as one flowering plant within the progeny of the stated parentage by the inventor in or about January 1990 in a controlled environment in De Kwakel.

The first asexual reproduction of Tersomka was accomplished when vegetative cuttings were taken from the initial selection in April 1990 in a controlled environment in De Kwakel, The Netherlands by a technician working under formulations established and supervised by the inventor. The new cultivar is presently being propagated by cuttings and tissue culture. Horticultural examination of selected units initiated in November 1990 has demonstrated that the combination of characteristics as herein disclosed for Tersomka are firmly fixed and are retained through successive generations of asexual reproduction.

Tersomka has not been observed under all possible environmental conditions. The phenotype may vary significantly with variations in environment such as temperature, light intensity and day length. The following observations, measurements and comparisons describe plants grown in commercial greenhouses in De Kwakel, The Netherlands under controlled conditions which closely typify those generally used in commercial practice.

The following traits have been repeatedly observed and have been determined to be basic characteristics of Tersomka, which in combination provide a new and distinct cultivar:

1. Single type flower and cup shaped flower form.
2. Ray florets are cream in color.
3. Dark purple disc florets.
4. Perianth lobe is cream in color.
5. The diameter of the flower head is relatively small, being approximately 70 mm.

Of the many commercial cultivars known to the present inventor, certain comparisons can be made with the new cultivar. The new cultivar Tersomka has a relatively small flower diameter (approximately 70 mm) and is similar in this characteristic, and also growth habit, to the cultivars Terkapol, Tertala and Terikatir, all cultivars of the present inventor disclosed in pending plant patent applications. However, Tersomka differs from the other cultivars in flower color and certain other characteristics. The flower color of Tersomka is somewhat similar to the flower color of the cultivar Sabrina. However, Sabrina has a much larger flower diameter of 10–11 cm, and there are other differences as well.

In comparison to the parent cultivars, the female parent M89.2 has a duplex to triplex flower type and flat flower form, a more yellow ray floret color, and a somewhat smaller diameter. The male parent M89.27 has single flower type and cupped flower form, cream ray florets and purple disc florets, and a larger (70–80 mm) flower diameter.

The accompanying photographic drawing shows typical inflorescence characteristics of Tersomka, with the colors being as nearly true as possible with illustrations of this type.

In the following description, color references are made to The Royal Horticultural Society Colour Chart (R.H.S.). The color values were determined at approximately 9:25 a.m. on Feb. 20, 1991 under natural light at De Kwakel, The Netherlands.

Classification:

*Botanical.*—*Gerbera jamesonii* cv Tersomka.

*Commercial.*—Gerbera.

Parentage: Seedling from cross of M89.2 and M89.27.

Plant: The plant when fully grown after approximately five (5) months of growth reaches a height of 40 cm, measured from the soil line.

Leaf blade:

*Length.*—Short.

*Width.*—Narrow.

*Blistering (puckering).*—Weak.

*Hairiness on upper side.*—Medium.

*Depth of cuts or incisions.*—Medium in central part of leaf.

*Color.*—Upper surface of leaf 137B; lower surface 138B.

*Glossiness on upper side.*—Weak.

*Angle at tip.*—Acute.

*Shape at tip.*—Pointed.
*Margin of lobes.*—Serrate.
*Extension of margin.*—Small.
*Petiole length.*—Medium.
*Petiole anthocyanin coloration.*—Present, strong in intensity.

Peduncle:
*Length.*—Medium.
*Cross section.*—Round, medium strength and thickness.
*Hairiness.*—Medium.
*Color.*—Medium green.
*Anthocyanin.*—Present at base, strong in intensity, none present at tip.
*Bracts.*—Absent.

Flower head:
*Type.*—Single; cup shaped in form.
*Diameter from edge to edge.*—Approximately 70 mm; varies somewhat depending on season and stage of development.
*Involucre.*—Height: Medium. Diameter: Small. Bracts: Longitudinal axis on inner rows are straight. Anthocyanin: Present.
*Ray florets.*—Number in outer row: 40–60. Length of floret: Less than 29 mm. Width of floret: 5–9 mm. Shape of floret: Generally elliptical with narrow base; longitudinal folding is weak. Shape of tip: Rounded, right angle, two incisions, very shallow in depth. Cross section of floret: Flat. Color distribution on inner side: Uniform. Striation: Absent. Claw spot: Absent. Color on top side: 159A. Color on bottom side: 10D. Color (general tonality from a distance of 3 meters: Cream.
*Disc florets.*—Diameter: 10–19 mm. Main color of perianth lobes: Cream. Color (mature and immature): Dark purple.

Reproductive parts:
*Stigma.*—Main color, white.
*Anthers.*—Main color, yellow; anthocyanin coloration absent.
*Pappus.*—Main color, purple.
*Style.*—Main color of distal part is white.

Disease resistance: Medium.
Pest resistance: medium.

I claim:

1. A new and distinct cultivar of Gerbera plant named Tersomka, as illustrated and described.

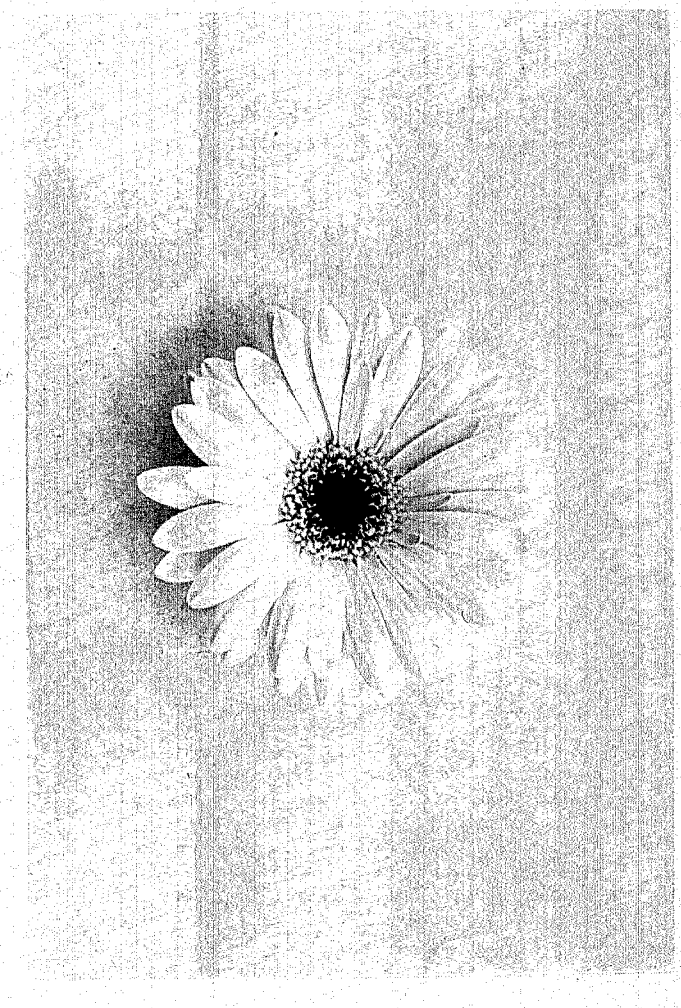

* * * * *